US011100373B1

(12) United States Patent
Crosby et al.

(10) Patent No.: US 11,100,373 B1
(45) Date of Patent: Aug. 24, 2021

(54) AUTONOMOUS AND CONTINUOUSLY SELF-IMPROVING LEARNING SYSTEM

(71) Applicant: DocBot, Inc., Irvine, CA (US)

(72) Inventors: Peter Crosby, San Juan Capistrano, CA (US); James Requa, Sherman Oaks, CA (US)

(73) Assignee: DocBot, Inc., Irvine, CA (US)

( * ) Notice: Subject to any disclaimer, the term of this patent is extended or adjusted under 35 U.S.C. 154(b) by 0 days.

(21) Appl. No.: 17/087,558

(22) Filed: Nov. 2, 2020

(51) Int. Cl.
*G06K 9/62* (2006.01)
*G06N 20/00* (2019.01)

(52) U.S. Cl.
CPC ......... *G06K 9/6268* (2013.01); *G06K 9/6228* (2013.01); *G06K 9/6256* (2013.01); *G06K 9/6261* (2013.01); *G06K 9/6262* (2013.01); *G06N 20/00* (2019.01)

(58) Field of Classification Search
CPC .. G06K 9/6268; G06K 9/6228; G06K 9/6256; G06K 9/6261; G06K 9/6262; G06N 20/00
See application file for complete search history.

(56) References Cited

U.S. PATENT DOCUMENTS

| 10,606,982 | B2 * | 3/2020 | Guo | G06F 40/169 |
| 10,671,934 | B1 | 6/2020 | Ninh et al. | |
| 2016/0210411 | A1 * | 7/2016 | Mentis | G16H 30/20 |

OTHER PUBLICATIONS

Desai, Sai Vikas, et al. "An adaptive supervision framework for active learning in object detection." arXiv preprint arXiv: 1908. 02454 (2019). (Year: 2019).*

(Continued)

*Primary Examiner* — Utpal D Shah
(74) *Attorney, Agent, or Firm* — Eversheds Sutherland (US) LLP; Nicola A. Pisano; Albert K. Heng

(57) ABSTRACT

A system and methods are provided in which an artificial intelligence inference module identifies targeted information in large-scale unlabeled data, wherein the artificial intelligence inference module autonomously learns hierarchical representations from large-scale unlabeled data and continually self-improves from self-labeled data points using a teacher model trained to detect known targets from combined inputs of a small hand labeled curated dataset prepared by a domain expert together with self-generated intermediate and global context features derived from the unlabeled dataset by unsupervised and self-supervised processes. The trained teacher model processes further unlabeled data to self-generate new weakly-supervised training samples that are self-refined and self-corrected, without human supervision, and then used as inputs to a noisy student model trained in a semi-supervised learning process on a combination of the teacher model training set and new weakly-supervised training samples. With each iteration, the noisy student model continually self-optimizes its learned parameters against a set of configurable validation criteria such that the learned parameters of the noisy student surpass and replace the learned parameter of the prior iteration teacher model, with these optimized learned parameters periodically used to update the artificial intelligence inference module.

14 Claims, 5 Drawing Sheets

(56) References Cited

OTHER PUBLICATIONS

Ahmed Mohammed, Ivar Farup, Marius Pedersen, Sule Yildirim, Øistein Hovde, "PS-DeVCEM: Pathology-sensitive deep learning model for video capsule endoscopy based on weakly labeled data", Computer Vision and Image Understanding, vol. 201, 2020 (Year: 2020).*

Berthelot et al., MixMatch: A Holistic Approach to Semi-Supervised Learning, 33rd Conference on Neural Information Processing Systems, NeurIPS 1-11 (2019).

Diba, et al., Weekly Supervised Cascaded Convolutional Networks, 10.1109/CVPR.2017.545 (201), retrieved from https://arxiv.org/abs/1611.08258v1.

Dietterich, et al., Solving the multiple-instance problem with axis-parallel rectangles, Artificial Intelligence, 89:31-71 (1997).

Doersch, et al., Unsupervised visual representation learning by context prediction, *Proceedings of theIEEE international conference on computer vision*, 2015, pp. 1422-1430.

Haussmann, Scalable Active Learning for Object Detection, arXiv:2004.04699 [es.CV] (2020), retrieved from https://arxiv.org/abs/2004.04699.

Ilse, et al., Attention-based Deep Multiple Instance Learning, Proceedings of the 35th International Conference on Machine Learning, Stockholm, Sweden, PMLR 80 (2018), retrieved from https://arxiv.org/abs/1802.04712.

Krizhevsky, et al., ImageNet Classification with Deep Convolutional Neural Networks, *Advances in Neural Information Processing Systems*, pp. 1097-1105 (2012).

Mahajan, et al., "Exploring the Limits of Weakly Supervised Pretraining," arXiv:1805.00932 [cs.CV], retrieved from https://arxiv.org/abs/1805.00932.

Rumelhart, et al., Learning internal representations by error propagation In: Parallel Distributed Processing: explorations in the microstructure of cognition, vol. 1: Foundations. MIT Press, Cambridge, MA, USA, Jan. 1986, pp. 318-362.

Rumelhart, et al., Learning representations by back-propagating errors, Nature, 323(9):533-536 (1986).

Xie, et al., Self-training With Noisy Student Improves ImageNet Classification, arXiv:1911.04252 [cs.LG] (2019), retrieved from http://arxiv.org/abs/1911.04252.

* cited by examiner

AUTONOMOUS AND CONTINUOUSLY SELF-IMPROVING LEARNING SYSTEM

I. FIELD OF THE INVENTION

This invention relates generally to the field of digital image processing, machine learning and computer predictive models, and more particularly to a system and methods for autonomously learning hierarchical representations from analysis of large-scale unlabeled raw data and continually self-improving detection capability using self-labeled data points.

II. BACKGROUND OF THE INVENTION

Machine learning is an application of artificial intelligence (AI) wherein systems have the ability to automatically learn and improve from experience without being explicitly programmed. Machine learning systems are used for a variety of applications including image analysis, speech recognition and detection of credit card fraud. As implied by the word "learning," the machine learns by training with real world examples to form deductions about newly presented information. For example, a machine learning system could be trained with several thousand images of content classified and labelled by a human observer, so that the content of a future previously unseen image can be deduced. This approach is referred to as "supervised learning" in that the machine learning is supervised by a human.

Previously known systems generally consist of two fundamentally different types of tasks in machine learning—unsupervised learning and supervised learning. The goal of supervised learning is to create a mapping from inputs to outputs (x to y), given a training set made up of input-output pairs (xi, yi). The core learning mechanism and fundamental building block of any supervised learning algorithm is "backpropagation," a method first popularized by Rumelhart et al, "Learning representations by back-propagating errors," Nature, 323(9):533-536 (1986). Backpropagation is the process of iteratively adjusting the parameters of a model (e.g., weights and biases) to minimize the prediction error. In the context of computer vision and image classification, one of the more influential successes of supervised learning was the publication of AlexNet, as described by Krizhevsky et al. in "ImageNet Classification with Deep Convolutional Neural Networks," Advances in Neural Information Processing Systems, 25, pp. 1097-1105 (2012). Since then, supervised learning has become a de facto standard for state of the art learning tasks.

Supervised learning systems provide potential solutions for many real-world computer vision problems, such as medical diagnosis and driving for autonomous vehicles. However, it is well known that the classification performance of a predictive model depends on the quality and quantity of training data. A major limitation of supervised learning in real-world applications is the difficulty in obtaining sufficient quality labeled data for training predictive models. Creating large amounts of labeled data is very costly and time-consuming. In addition, any dataset used for training a machine learning system is susceptible to errors including noise (such as variation in labelling of the same images by different observers), errors in labelling and sparseness (i.e., not all image types have a curated label), which in turn propagate errors in the output of the machine learning system. Thus, while supervised learning algorithms are capable of addressing many real-world problems, their dependence on quality hand-labeled data that is time-consuming and expensive to obtain, limits the utility of such solutions.

In contrast, unsupervised machine learning systems require a training dataset that is neither classified nor labeled. Instead, the goal of unsupervised learning systems is to infer a function that describes a hidden structure from unlabeled data. The system does not generate a specific desired output, but rather explores the data and draws inferences from datasets to illuminate naturally occurring structures hidden within unlabeled data.

More particularly, unsupervised learning attempts to find interesting structure and/or patterns in data without any assigning labels or pre-defined ground-truth. Examples of traditional unsupervised learning include clustering, outlier detection, and dimensionality reduction. In the context of computer vision, one of the early successes of unsupervised learning is autoencoders. The goal of autoencoders is simply to transform inputs into outputs with the least possible amount of distortion. Autoencoders were first introduced in the 1980s by Rumelhart et al. in "Learning Internal Representations By Error Propagation," Parallel Distributed Processing: Explorations in the Microstructure of Cognition: Foundations, 318-362, MIT Press publisher (1987) to address the problem of "backpropagation without a teacher", in which the input data is employed as the teacher. While traditional unsupervised learning techniques are useful for extracting valuable insights from unlabeled data, these solutions alone do not provide a means for self-learning outputs as they lack any discriminating input-output pairs and hence cannot be used alone to solve predefined tasks.

In recent years, within the context of unsupervised learning, the concept of "self-supervised learning" has emerged. Self-supervised learning tasks (often referred to as "pretext tasks") can be assigned for processing unlabeled data by using a supervised learning algorithm to learn and predict intermediate labels that are mapped to intermediate representations derived directly from the unlabeled data. Self-supervised learning systems typically are used in combination with supervised learning systems to reduce dependency on large-scale labeled datasets, which are required for supervised learning systems. The intermediate representations correspond to sub-tasks of a final task and can accelerate the supervised learning process, as well as improve generalizability to unseen data.

Examples of self-supervised learning methods are described by Doersch et al. in "Unsupervised visual representation learning by context prediction," Proceedings of the IEEE International Conference on Computer Vision, 2015, 1422-1430. Additionally, Facebook AI, led by Chief AI Scientist Yann LeCunn has widely promoted usage of self-supervised learning to accelerate the process of identifying content violations on the FaceBook platform across multiple content modalities including images, NLP, audio/speech, and videos, as described in Mahajan et al., "Exploring the Limits of Weakly Supervised Pretraining," arXiv: 1805.00932 [cs.CV] (2018), retrieved from http://arxiv.org/abs/1805.00932. While self-supervised learning as a precursor to supervised-learning tasks advantageously leverages large-scale use of unlabeled data for training supervised learning systems, the combination of these learning systems alone falls short of providing an autonomous and continuously self-improving learning system because it provides no continuous self-learning component beyond the supervised learning task.

Semi-supervised learning (SSL) systems represent a middle ground between supervised and unsupervised learning, and use both labeled and unlabeled data for training. Typically, such systems employ a small amount of labeled data (referred to as a "curated dataset") and a large amount of unlabeled data. Combining learning modalities can considerably improve learning accuracy. In particular, SSL is a promising method for leveraging unlabeled data by training the system with a hand-labeled curated dataset alongside a much larger unlabeled dataset, which includes self-generated annotations that are used as weakly supervised noisy labels.

The semi-supervised learning process typically consists of initially training a supervised learning algorithm on a small-labeled dataset as a gold standard for ground-truth mapping of input-output pairs. The trained supervised algorithm then is used to assign weakly supervised labels (sometimes referred to as "pseudo labels") to a much larger unlabeled dataset known to contain examples of the targets in the labeled dataset. Finally, the supervised learning algorithm is trained on the combined sets of hand-labeled and pseudo-labeled data in a semi-supervised fashion.

While the concept of semi-supervised learning methods had been proposed in the early 1960s, this approach was not widely successful until 2019, when researchers from Google proposed a unification of dominant semi-supervised learning methods. As described by Berthelot et al., "MixMatch: A Holistic Approach to Semi-Supervised Learning," 33rd Conference on Neural Information Processing Systems (NeurIPS 1-11, 2019), that method achieved state-of-the-art results by reducing previous best error rates by a factor of four. Semi-supervised learning thus shows great promise in leveraging large-scale unlabeled data to reduce dependency on large amounts of hand-labeled data, while achieving a good accuracy-speed tradeoff. However, the results of those solutions alone do not yet surpass the performance and precision of fully supervised learning methods. Additionally, without careful human on-hands observation, these learning systems are highly susceptible to overfitting both to variance in the training data (i.e., noise and outliers) and in other cases continually amplifying biases to oversimplified assumptions about the target (i.e., positive feedback loops). In view of these limitations, semi-supervised learning alone cannot provide a reliable autonomous and continuously self-improving learning system.

A further advance beyond semi-supervised learning, as described above, is the method of "noisy student" self-training proposed by researchers at Google Brain in late 2019, Xie et al., "Self-training with Noisy Student improves ImageNet classification," arXiv:1911.04252 [cs.LG] (2019), retrieved from http://arxiv.org/abs/1911.04252). The noisy student self-training approach achieves state-of-the-art accuracy on ImageNet, a popular machine learning benchmark dataset. This method improves upon previously known semi-supervised learning methods by continually updating a teacher model with improvements learned by a noisy student trained on semi-supervised data. Drawbacks of the noisy student approach include (1) it lacks a mechanism for self-supervised learning of pretext tasks on unlabeled data; (2) lacks a way for self-cleaning unlabeled data, self-selecting and self-refining weakly supervised labels; and (3) lacks self-verification.

Given that semi-supervised learning techniques continue to rely on hand-labeling a subset of the unsupervised training data, data efficiency is a key challenge that emerges for how best to select data instances for hand-labeling. Active learning (AL) is a technique that can improve data efficiency by selecting instances for training a machine-learning algorithm that optimally contributes to improvements in performance on the targeted task. Researchers from NVIDIA proposed a technique for active learning for improving object detection for autonomous vehicles, as described in Haussmann, et al., "Scalable Active Learning for Object Detection," arXiv:2004.04699 [cs.CV] (2020), retrieved from https://arxiv.org/abs/2004.04699. As proposed in that paper, AL allows a learning algorithm effectively to choose for itself which data instances to label from the pool of unlabeled data, based on criteria such as which images cause the highest level of uncertainty for the algorithm. The benefit of relying on AL in the learning process is that data selection, normally a very labor-intensive manual process, becomes largely automated. This is accomplished by allowing the algorithm to choose data instances that contribute to improving the model's performance, which is a difficult task even for a human with sufficient domain knowledge of the targeted task. While AL may be beneficial, that process still requires continual hand labeling of new data instances selected by the AL process.

Multiple instance learning (MIL) is a variation of supervised learning, sometimes referred to as "weakly-supervised" learning. In this process, multiple data points are assigned one group label. In contrast to supervised learning, where each individual data point is assigned a discrete label, in MIL there is no one-to-one mapping of labels for each instance. Instead, typically due to having incomplete information, a "bag" of instances is assigned one coarse-grained annotation. For example, if the data to be analyzed consists of a colonoscopy procedure video feed, the multiple data points may correspond to individual frames of the video. Using MIL, a single label could be assigned for the entire video, for example whether there are any pre-cancerous polyps detected in the entire video, as opposed to whether such polyps are detected in any individual frame. In this example, if at least one of the video frames in the colonoscopy contained a polyp, then the entire video would be assigned a positive label; a negative label would be assigned only if no frame contained polyps.

The term "multiple-instance learning" was introduced in mid-1990 for drug discovery prediction, as described in Dietterich, et al., "Solving the multiple-instance problem with axis-parallel rectangles." Artificial Intelligence 89:31-71 (1997). More recently, researchers at the University of Amsterdam proposed applying MIL to medical imaging, as described in Ilse, et al. "Attention-based Deep Multiple Instance Learning," Proceedings of the 35th International Conference on Machine Learning, Stockholm, Sweden, PMLR 80, 2018, retrieved from https://arxiv.org/abs/1802.04712. MIL also been applied in the second stage of object detectors as a method for selecting key instances from object proposal regions-of-interest ROIs, as described in Diba et al., "Weakly Supervised Cascaded Convolutional Networks," 10.1109/CVPR.2017.545 (201), retrieved from https://arxiv.org/abs/1611.08258v1.

MIL has shown benefit in applications where training data is limited because fine-grained annotations are extremely labor-intensive and costly to obtain, such as a dermatopathologist hand-labeling cancerous cells on a molecular-level from gigapixel whole slide images. Accordingly, MIL advantageously leverages incomplete information that is much more cost-effective to obtain, such as having a dermatopathologist assign a single label to a whole slide image as cancerous or not, and then having the MIL algorithm identify which cells contribute to that pathology label. However, the metrics presented by the foregoing research show that when used on its own as the primary source for a model learning process, MIL falls short of supervised learning approaches. This is due to the large gap in the quality of the coarse-grained weakly supervised annotations when compared to curated annotations.

As discussed above, a main obstacle for SSL methods is error handling of noisy labels. This is so because repeated inclusion of mislabeled data amplifies errors and negatively impacts the performance of the system. While SSL methods that employ human supervision for label correction are effective and less time-consuming than fully supervised learning methods, such systems are not fully scalable because manually confirming correct or identifying incorrect labels creates a time-consuming bottleneck to the self-labeling and self-training process. While fully scalable SSL methods exist that do not rely on human supervision, performance is less effective.

It would be desirable to train classifiers with diverse labeled data that fully represents all targeted tasks. In many domains, there is an abundant unlabeled data, but obtaining a representative subset is very challenging because the data typically is noisy and sparse. Although there is essentially no limit to the availability of unlabeled data, most supervised learning methods are not designed to leverage unlabeled data and accordingly the learning process is unable to scale efficiently.

In view of the foregoing, there exists a need to automate the label correction process without human supervision. It therefore would be desirable to provide an autonomous and continually self-improving learning system that is fully scalable, low-cost, time-efficient, and highly effective in its performance.

III. BRIEF DESCRIPTION OF THE DRAWINGS

IV. SUMMARY OF THE INVENTION

Figure 1:
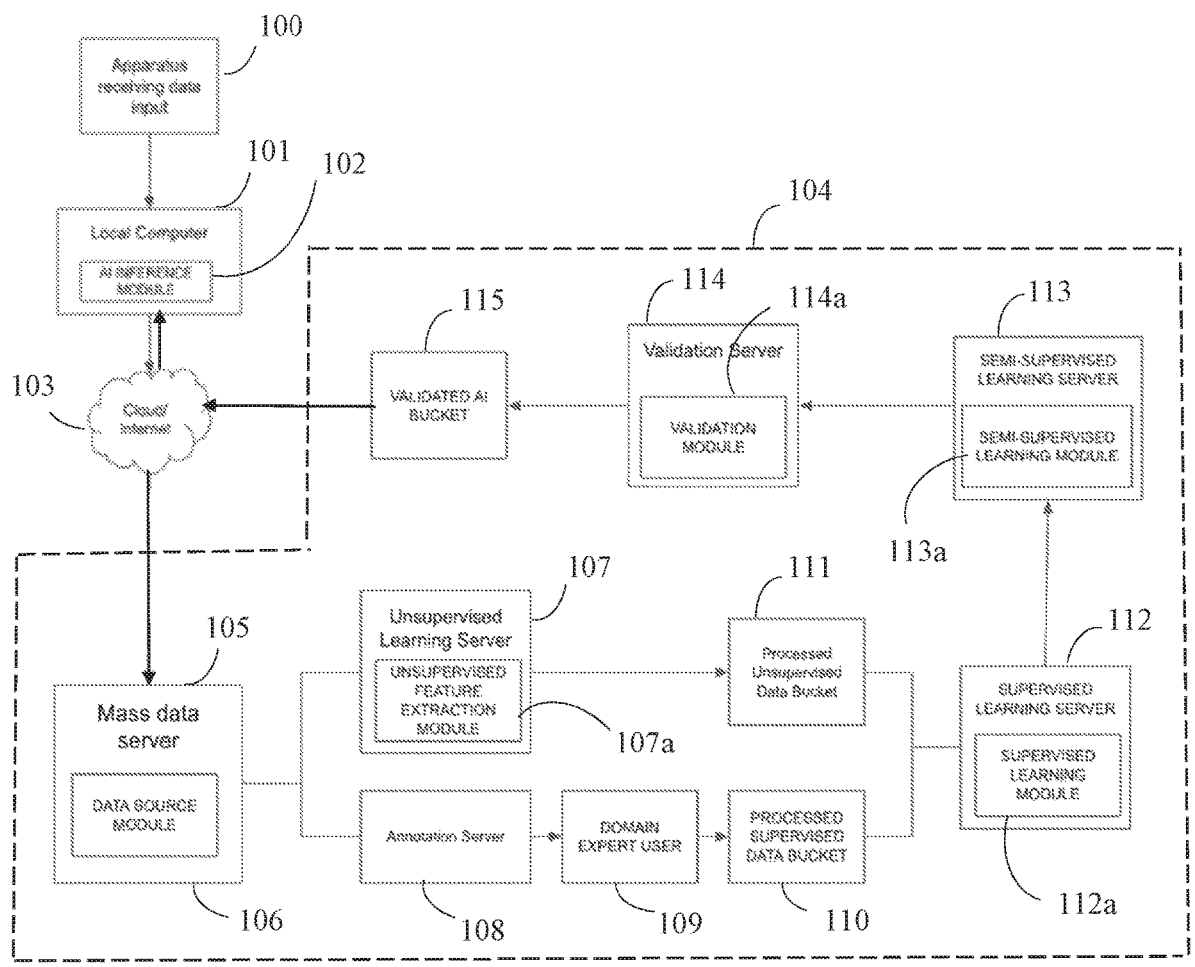
FIG. 1 is a schematic diagram of a system implementing the autonomous and continuously self-improving system of the present invention.

In view of the foregoing drawbacks of the previously known systems, the present invention is directed to a configurable system for self-analyzing, self-cleaning, and self-extracting features from unlabeled data to provide a continually self-improving learning system for predictive modeling of predefined targets. In an exemplary embodiment of the invention, an artificial intelligence ("AI") inference module for extracting desired features from an input stream resides on a local computer. Apparatus, such as an endoscopy or colonoscopy system associated with the local computer provides a data stream, e.g., video output, that serves as input feed to the AI inference module running on the local computer. The AI inference module analyzes the input feed and generates annotations for the user of the local computer, e.g., which may take the form of annotations in a display of the video output presented to the apparatus user, to signal detection in the video output of potential abnormalities, such as polyps.

In accordance with the foregoing exemplary embodiment of the present invention, the video output from the procedure is uploaded to a remote server that is programmed with the continually self-improving learning system of the present invention, such that the video output serves as an additional dataset for training of the continually self-improving system. Analysis of the new video output data may generate additional learned features that improve the unsupervised learning capability of the AI inference module. The AI inference module then is updated at the local computer for use in subsequent procedures or re-evaluation of the recorded video output to improve accuracy of the results generated by the preceding instantiation of the AI inference module at the local computer.

In accordance with one aspect of the invention, a method is provided for self-analyzing and self-extracting features from large-scale unlabeled data for use in self-learning, without human supervision. The method involves a series of unsupervised feature extraction processes, including self-supervised pretext task learning and cleaning/grading, which extract a set of self-learned micro-level and macro-level features/parameters. Those micro- and macro-level features provide intermediate and global context features representative of the unlabeled dataset. The learned features from the unsupervised processes are applied to self-cleaned, self-graded unlabeled data before being sent as inputs to a semi-supervised self-learning process.

In another aspect of the invention, a method is provided for generating representative labels for self-learning based on analysis of large amounts of unlabeled data, without human supervision. The method involves combining a model pre-trained by supervised learning methods with self-learned features extracted from unlabeled data to generate self-annotated labels from new unlabeled data. The new unlabeled data then is subjected to a self-selection, self-correction, and self-refinement process that results in high quality weakly supervised labels for self-learning.

In a further aspect of the invention, a method is provided for self-approval of improved learned parameters, without human intervention, thereby providing an autonomous continual learning optimization process. The method involves running a noisy student model, self-trained in a semi-supervised learning process, on a validation test set. The result of that analysis is a group of validation metrics that are self-checked against predefined criteria for a pass/fail result. In this manner, the pass/fail result causes the learned parameters being used to generate new-labeled data points from unlabeled data, for further iterations of self-learning and self-optimization of targeted tasks, or the learned parameters are self-rejected and sent for error-correction analysis.

As described for the exemplary embodiment above, the autonomous continual learning optimization process may be conducted on a distributed network that includes a local computer and one or more remote servers connected by a wide area network or the Internet. The local computer is disposed near the point of origin of the data to be analyzed and is programmed with an inference module for analyzing the locally generated data. Data from the local computer periodically may be sent to, and aggregated with, a much larger data store that is employed to improve the detection capability of the learning process. The inference model at the local computer periodically or continually is updated to reflect improvements in the detection efficiency and accuracy autonomously developed on the one or more remote servers.

V. DETAILED DESCRIPTION OF THE PREFERRED EMBODIMENTS

Referring to FIG. 1, exemplary system 10 constructed in accordance with the principles of the present invention is described. In this disclosure, exemplary system 10 is configured to detect potential abnormalities in a video feed generated during an endoscopy or colonoscopy examination, although the present invention advantageously may be employed in any other endeavor where an autonomous and continually improving self-learning system is desired. In accordance with this exemplary system, apparatus 100, such as an endoscopy or colonoscopy system, generates a video feed for local computer 101.

The video output generated by apparatus 100 constitutes the input data feed that is analyzed by Artificial Intelligence (AI) Inference Module 102 that executes on local computer 102. Illustratively, if apparatus 100 is a colonoscope, the input data feed to local computer 101 and AI inference module 102 is the stream of video images generated by the colonoscope camera. In one preferred embodiment, AI Inference Module 102 analyzes the input data feed in near real time and generates predictions regarding the presence of tissue abnormalities, e.g., polyps or fissures, in the video images. As described in commonly assigned U.S. Pat. No. 10,671,934, such detections may be displayed on a video screen for the clinician's review and consideration during the colonoscopy procedure.

Local computer 101 may be one of several local computers, each of which is connected to a corresponding apparatus 100, and is programmed to upload via a wide area network, such as Internet 103, the video record dataset for each completed colonoscopy procedure to remote server system 104, which include mass data storage 105. Data storage 105 serves as a repository for all of the completed datasets 106, and makes datasets 106 accessible to the continuously self-improving learning system of the present invention. In particular, data storage 105 is accessible to unsupervised learning server 107 for processing by unsupervised feature extraction model 107a and annotations Server 108. Annotations server 108 is accessible to domain expert users 109 for the purposes of annotating images within the datasets to identify known targets. For example, a domain expert user may be a gastroenterologist and the targeted task could be detecting colon polyps. Processed annotations, when completed, are uploaded to processed supervised data bucket 110, and this data is used for training the supervised learning model as described below.

Data processed by unsupervised feature extraction module 107a are uploaded to processed unsupervised data bucket 111 upon completion of analysis. Data in both processed supervised data bucket 110 and processed unsupervised data bucket 111 and are accessible by supervised learning server 112 for analysis by supervised learning module 112a. Data processed by supervised learning module 112a are accessible by semi-supervised learning server 113 for processing by semi-supervised learning module 113a. Data processed by semi-supervised learning server 113 are accessible by validation server 114 for processing by validation module 114a, which in turn uploads validated module information to validated AI bucket 115. The module information made available in validated AI bucket 115 finally is made accessible by local computer 101 to update the AI Inference Module running on the computer. As will be understood by a person of skill in the art of machine learning, the information in validated AI bucket 115 is not detection results specific to any particular dataset uploaded to mass data storage 105, but instead consists of the learned features and parameters that determine the accuracy of the detection capability of the AI Inference Model.

Figure 2:
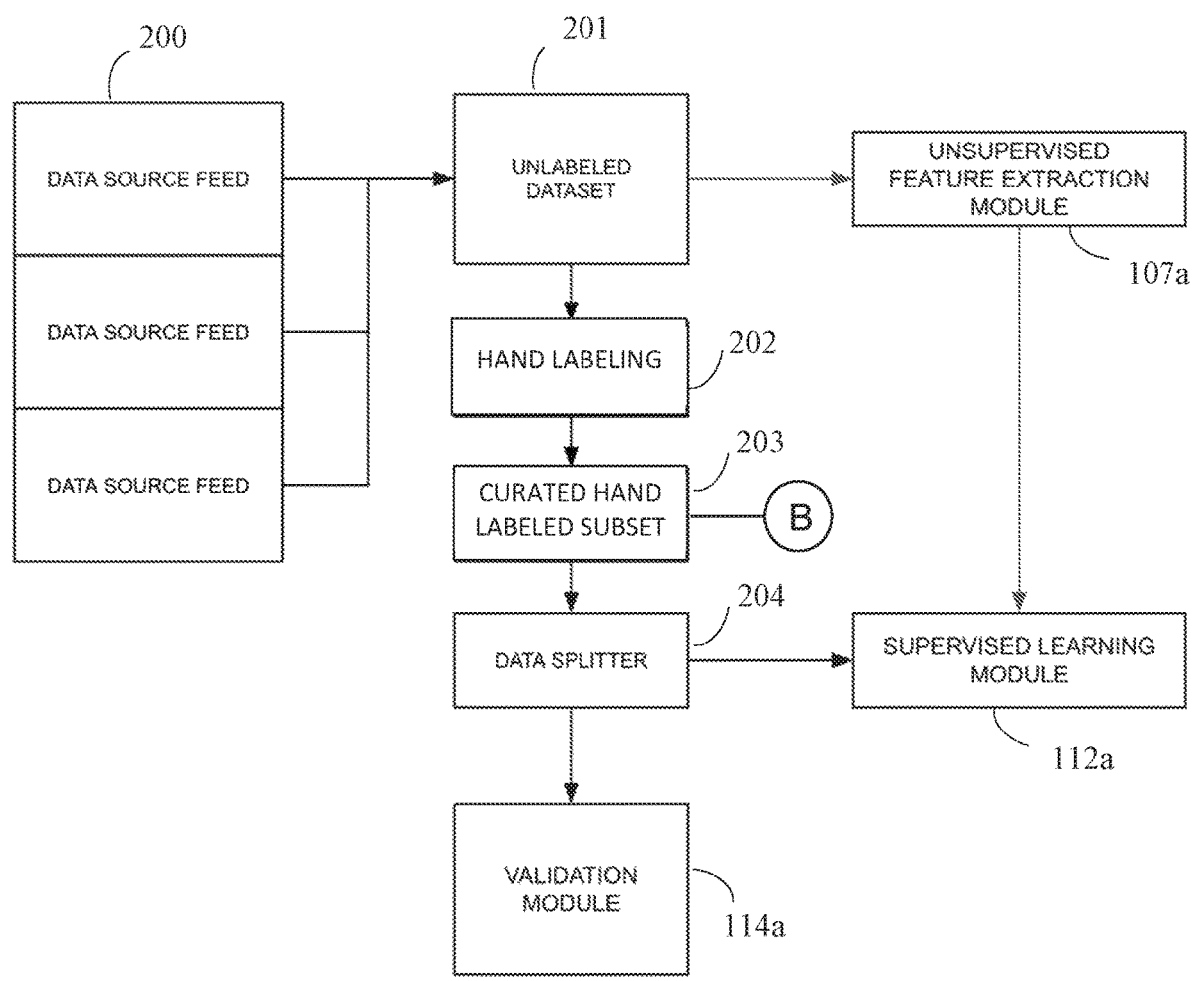
FIG. 2 is a schematic illustration of data flows within inventive system.

Referring now to FIG. 2, flow of data through remote server 104 is described. In particular, multiple datasets 200 are stored on mass storage 105 described in FIG. 1. A particular dataset selected from mass data storage 105 initially consists of unlabeled data 201. A subset of unlabeled data 201 may be partitioned for processing by annotation server 108. More specifically, the subset of dataset 200 processed by annotation server 108 is reviewed by one or more domain expert users 109 with domain expertise for the target label(s) in hand labeling step 202; completion of the hand labeling task results in curated hand labeled subset 203. Additional curated hand labeled data may be accessible at step 203 via validation module 114a, as described with respect to FIG. 5. In the exemplary colonoscopy embodiment, the dataset could be a recorded continuous video feed from a colonoscopy machine, and the individual with domain expertise could be a gastroenterologist with experience in interpreting colonoscopy images. The labeled curated dataset may be further partitioned at data splitter step 204, with a portion of curated dataset 203 being made accessible to supervised learning module 112a via processed supervisor bucket 110, and the remainder of the subset being reserved for use by validation module 114a. The entire unlabeled dataset 201 also is processed by unsupervised feature extraction module 107a, as described with respect to FIG. 3 below.

Figure 3:
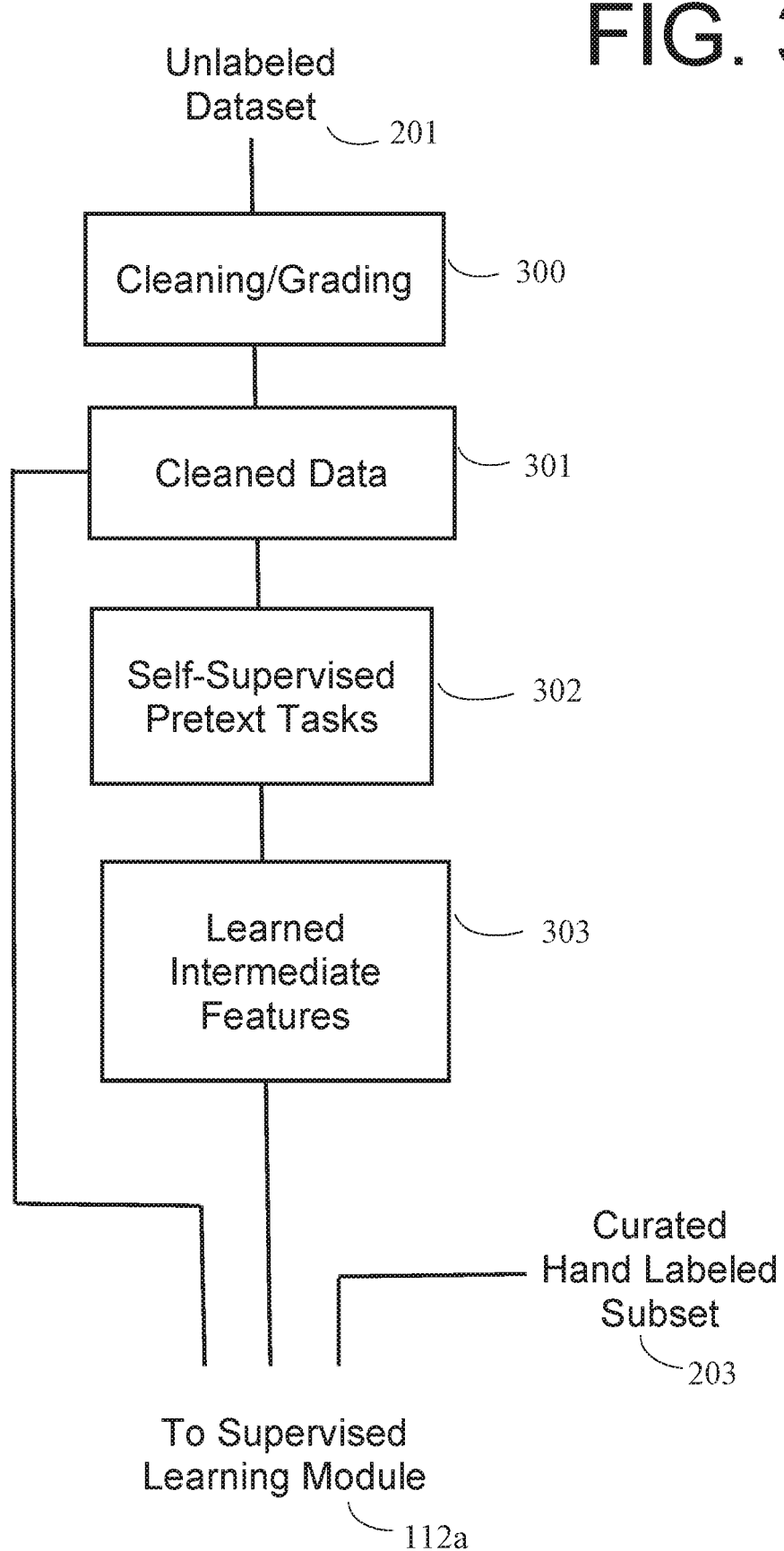
FIG. 3 illustrates the flow of data through the unsupervised feature extraction module and the supervised feature extraction module of the system of FIG. 1.

Turning now to FIG. 3, operation of unsupervised feature extraction module 107a is described. Unsupervised feature extraction module 107a includes two modules that perform unsupervised feature extraction processes: cleaning and grading module 300 that outputs cleaned data 301, and self-supervised pretext task learning 302 that generates learned intermediate features 303. The outputs from the unsupervised feature extraction module, learned intermediate features 303 and clean unlabeled data 301 then are used as inputs supervised learning module 112a.

Cleaning and grading module 300 analyzes the data in unlabeled dataset 201 to determine if the data meets certain minimum criteria to be usefully analyzed by the self-supervised pretext task-learning module 302. In particular, a grading analysis is performed on unlabeled dataset 201 that filters the unlabeled data and generates as an output cleaned data 301. For example, in the context of an exemplary colonoscopy detection system embodiment of the invention, the unlabeled data may consist of a video feed from a colonoscopy. The unlabeled data could be determined to be "clean" by an algorithm trained to classify frames for visual clarity and "graded" by an algorithm trained to assign a prep score for colonoscopy.

A self-supervised learning process then is applied to cleaned data 301 to generate intermediate representations of the unlabeled dataset by learning to predict on a set of predefined pretext tasks. For example, if the data consists of a video feed of a colonoscopy, each frame in the video feed could be converted into a grid of tiles, and then locations of the tiles randomly rearranged. The pretext task could consist of reordering the correct positions of the tiles to recreate the original frame, for example, by analyzing color intensities along the edges of the tiles. Another pretext task could reorder in correct sequence of a shuffled sequence of video frames. Other pretext tasks will be apparent to persons of ordinary skill in the machine-learning field. These pretext tasks have in common that they do not require hand labeling, but instead, the target label is derived directly from the inherent data structure. The output of the self-supervised learning process is a set of self-learned features/parameters that are representative of unlabeled dataset 301. Those skilled in the art of machine learning will recognize that the learned parameters can be re-used to initialize learning a new task in a process, referred to as transfer learning. The features learned by conducting the pretext tasks on unlabeled data may be used in a similar manner.

Figure 4:
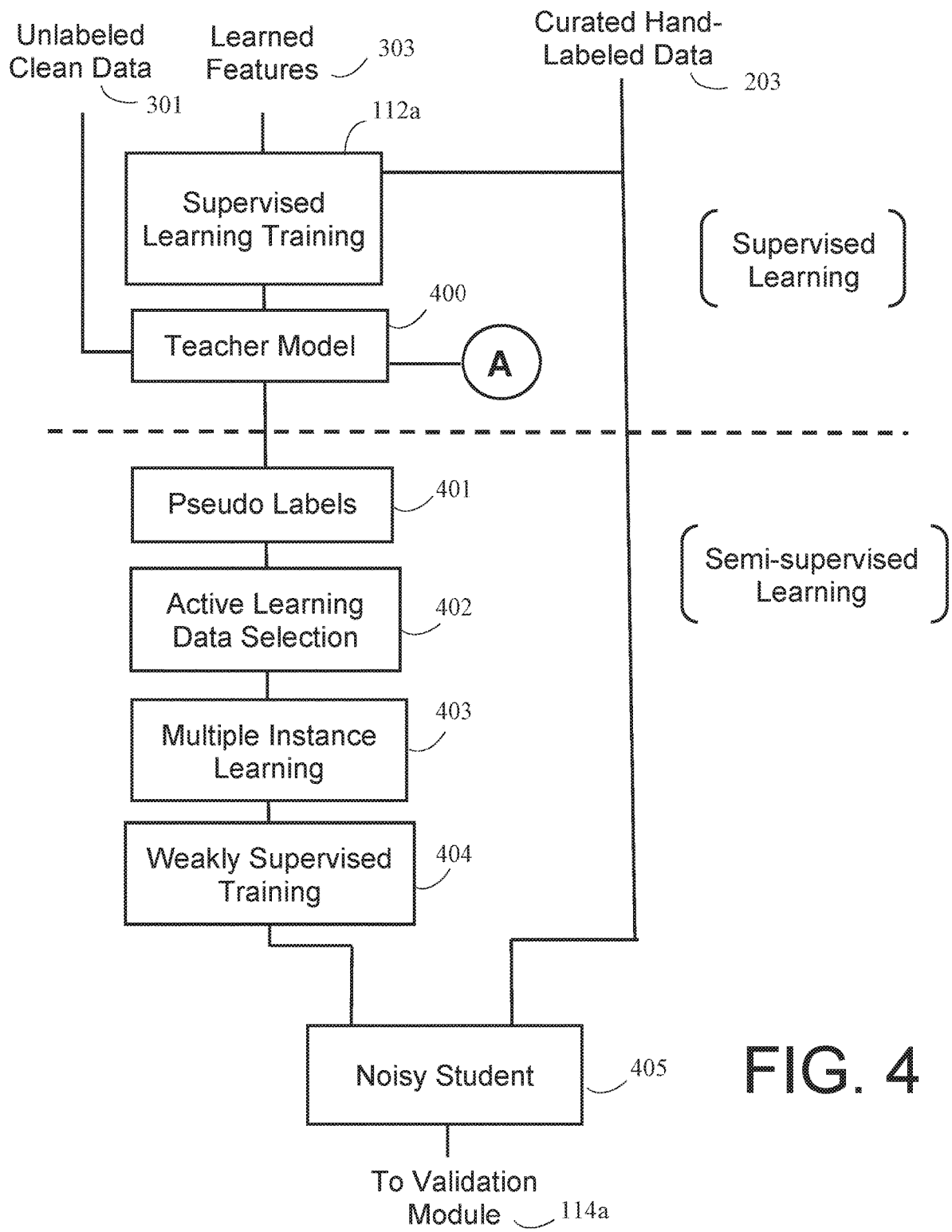
FIG. 4 illustrates the flow of data through the supervised learning and semi-supervised learning modules of the system of FIG. 1.

Referring now to FIG. 4, operation of supervised learning module 112a and semi-supervised learning module 113a is described. In supervised learning module 112a, the learned features from the unsupervised feature extraction module 107a and the curated training subset are used to train a teacher model to learn known targets, resulting in teacher model 400 with learned parameters. Teacher model 400 with its trained learned parameters then is used to generate outputs (i.e. predictions) from the cleaned unlabeled data for further processing by semi-supervised learning module 113a. In particular, teacher model 400 first generates as outputs pseudo labels 401, which are predictions or extracted features from processing the clean unlabeled data. Teacher model 400 also may be updated to employ the learned parameters of noisy student model 405 if the student model successfully meets performance criteria when checked by validation module 114a, as described below.

Next, in semi-supervised learning module 113a, active learning (AL) process 402 selects data points from the pseudo-labeled data based on predefined criteria. For example, the data instances may be auto-selected based on a level of uncertainty in the model's predictions. In the context of the colonoscopy detection embodiment, if the input data consists of individual frames from a colonoscopy video feed and the output of teacher model 400 includes bounding boxes and probabilities representing confidence levels of the predictions of features identified in the image frames, such as colon polyps, AL process 402 may auto-select image frames based on the level of uncertainty in the predictions.

Following AL process 402, multiple instance learning (MIL) process 403 is performed on the selected data points to further self-select, self-correct, and self-refine the highest quality weakly supervised labels. For example, if AL process 402 selects a "bag" of image frames with assigned bounding boxes and probabilities representing the presence of preselected features, such as colon polyps, in each of the instances in the bag, then MIL process 403 selects the key instances in the bag that best represent the bag's assigned pseudo-label.

Upon completion of the pseudo labelling, AL and MIL selection processes 401-403, weakly supervised training process 404 is performed to train and improve processes 401, 402 and 403. In particular, weakly supervised training process 404 learns parameters for AL process 402 to enable selection of new data instance proposals for continual learning that are most likely to contribute positively to algorithm performance. Similarly, MIL process 403 is trained to provide error-correction and noise-suppression by learning to suppress predictions that most likely are incorrect, while more heavily weighting those predictions that most likely are correct predictions, despite the assignment of a low confidence level by teacher model 400. Processes 401-403, together with weakly supervised training process 404, enable the addition of new training data instances in a fully automated and scalable way, without the labor-intensive manual processing of data selection or label error correction typically performed by humans.

The weakly supervised labeled data points generated for the unlabeled dataset then are combined with labeled data points from the curated dataset to create noisy student predictive model 405. Noisy student model 405 employs not only learned parameters inherited from the teacher model, but also employs additional learned parameters determined by the weakly supervised training process 404. Additional predictions generated by noisy student 405 for unlabeled data and its learned parameters are validated by validation module 114a.

Figure 5:
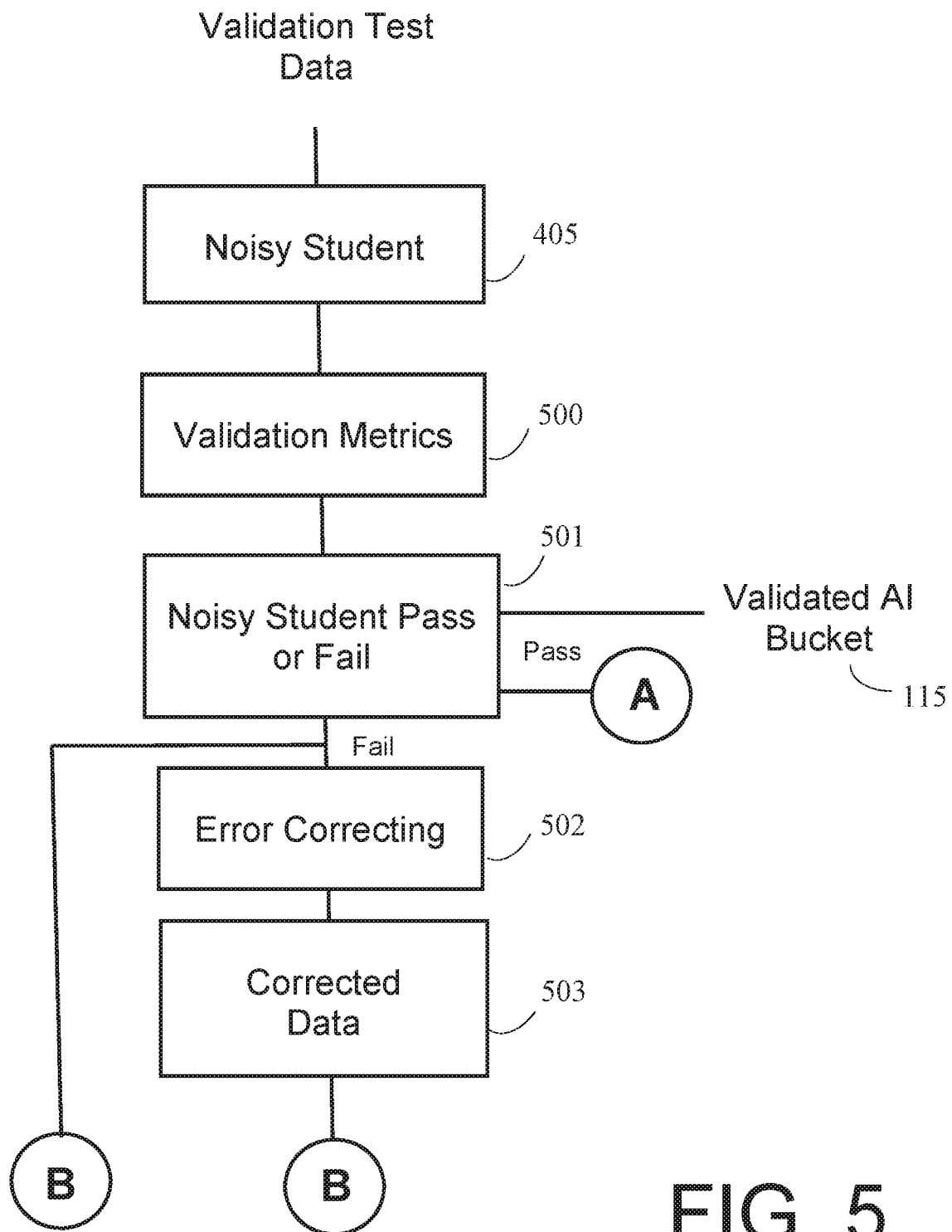
FIG. 5 illustrates the flow of the data through the validation module of the system of FIG. 1.

Turning now to FIG. 5, noisy student model 405 is run on validation test data, which is a subset of the curated dataset set aside for validation purposes, as determined by data splitter 204 in FIG. 2. Noisy student model 405 generates predictions and validation metrics 500, which are checked against predefined criteria for pass/fail result 501. If the validation metrics meet the pass criteria, the noisy student learned parameters might be uploaded to teacher model 400 of supervised learning module 112a for processing of new unlabeled data points. In addition, the noisy student model learned parameters are made available in validated AI bucket 115 to be transmitted to the AI inference module 102 of local computer 101.

Still referring to FIG. 5, if the validation metrics for a current iteration do not meet the pass criteria, the outputs of the noisy student may be sent for error-correction analysis 502, e.g., for review and correction by a domain expert user. Alternatively, noisy student 405 may be trained on additional datasets 200 without invoking domain expert user intervention. It is expected that noisy student 405, and correspondingly teacher model 400, will gradually improve in accuracy as its learned parameters reflect increasingly larger amounts of data, thus permitting a corresponding reduction in the manual effort to domain expert users to perform error correction. The outputs of the error-correction process include corrected data points 503 which further be employed as inputs to succeeding iterations of semi-supervised learning module 113a and/or the results of which may be used with unsupervised feature extraction module 107a for additional or new unsupervised feature extraction tasks.

While preferred illustrative embodiments of the invention are described above, it will be apparent to one skilled in the art that various changes and modifications may be made therein without departing from the invention, and the appended claims are intended to cover all such changes and modifications that fall within the true spirit and scope of the invention.

What is claimed:

1. Apparatus for self-improving the classification of features detected in an image dataset, the apparatus comprising:
    memory for storing instructions; and
    at least one processor to execute the instructions to:
        partition the dataset into a first subset and a second subset;
        receive from a domain expert user a curated dataset based on review of the first subset;
        extract learned intermediate features from the second subset using self-supervised pretext tasks;
        train a teacher model using the learned intermediate features and the curated dataset;
        execute the teacher model to generate pseudo labels for the second subset;
        apply an active learning process to select a subset of the pseudo labels;
        apply a multiple instance learning process to the subset of pseudo labels to generate a reduced subset of pseudo labels;

employ a weakly supervised training process to train a noisy student model using the reduced subset of pseudo labels to generate a set of learned parameters for classification of detected features; and validate the set of learned parameters.

2. The apparatus of claim 1, wherein the instructions further comprise instructions for cleaning and grading data within the second subset after partitioning the dataset.

3. The apparatus of claim 1, wherein the instructions further comprise, during validation of the set of learned parameters, comparing an accuracy of classification of detected features against at least a portion of the curated dataset.

4. The apparatus of claim 1, wherein the instructions further comprise, during validation of the set of learned parameters, identifying a portion of the reduced subset of pseudo labels for error correction by a domain expert user.

5. A system for classifying features detected in an image dataset, the system comprising:
   apparatus for generating a stream of video data;
   a local computer having an AI inference module for analyzing the video data to detect and identify potential abnormalities;
   a remote server coupled to the local computer via a wide area network to receive the video data, the remote server comprising
   memory for storing instructions and the video data; and
   at least one processor to execute the instructions to:
      partition the video data into a first subset and a second subset;
      receive from a domain expert user a curated dataset based on review of the first subset;
      extract learned intermediate features from the second subset using self-supervised pretext tasks;
      train a teacher model using the learned intermediate features and the curated dataset;
      execute the teacher model to generate pseudo labels for the second subset;
      apply an active learning process to select a subset of the pseudo labels;
      apply a multiple instance learning process to the subset of pseudo labels to generate a reduced subset of pseudo labels;
      employ a weakly supervised training process to train a noisy student model using the reduced subset of pseudo labels to generate a set of learned parameters for classification of detected features;
      validate the set of learned parameters; and
      periodically transmit the set of learned parameters to the local computer to update the AI inference module.

6. The system of claim 5, wherein the instructions further comprise instructions for cleaning and grading data within the second subset after partitioning the video data.

7. The system of claim 5, wherein the instructions further comprise, during validation of the set of learned parameters, comparing an accuracy of classification of detected features against at least a portion of the curated dataset.

8. The system of claim 5, wherein the instructions further comprise, during validation of the set of learned parameters, identifying a portion of the reduced subset of pseudo labels for error correction by a domain expert user.

9. The system of claim 5, wherein the apparatus for generating a stream of video data comprises an endoscope.

10. A system for classifying features in a video stream output by a colonoscope, the system comprising:
    a local computer having an AI inference module coupled to colonoscope for analyzing a video stream to detect and identify potential abnormalities;
    a remote server coupled to the local computer via a wide area network to receive and store the video stream, the remote server comprising
    memory for storing instructions and the video stream; and
    at least one processor to execute the instructions to:
       partition the video stream into a first subset and a second subset;
       receive from a domain expert user a curated dataset based on review of the first subset;
       extract learned intermediate features from the second subset using self-supervised pretext tasks;
       train a teacher model using the learned intermediate features and the curated dataset;
       execute the teacher model to generate pseudo labels for the second subset;
       apply an active learning process to select a subset of the pseudo labels;
       apply a multiple instance learning process to the subset of pseudo labels to generate a reduced subset of pseudo labels;
       employ a weakly supervised training process to train a noisy student model using the reduced subset of pseudo labels to generate a set of learned parameters for classification of detected features;
       validate the set of learned parameters; and
       periodically transmit the set of learned parameters to the local computer to update the AI inference module.

11. The system of claim 10, wherein the instructions further comprise instructions for cleaning and grading data within the second subset after partitioning the video stream.

12. The system of claim 10, wherein the instructions further comprise, during validation of the set of learned parameters, comparing an accuracy of classification of detected features against at least a portion of the curated dataset.

13. The system of claim 10, wherein the instructions further comprise, during validation of the set of learned parameters, identifying a portion of the reduced subset of pseudo labels for error correction by a domain expert user.

14. The system of claim 10, further comprising a colonoscope for generating the video stream coupled to the local computer.

* * * * *